US00PP31704P2

(12) United States Plant Patent
Wood

(10) Patent No.: US PP31,704 P2
(45) Date of Patent: Apr. 28, 2020

(54) ***JUNIPERUS* PLANT NAMED 'SMNJCHM'**

(50) Latin Name: *Juniperus chinensis*
Varietal Denomination: SMNJCHM

(71) Applicant: Timothy D Wood, Spring Lake, MI (US)

(72) Inventor: Timothy D Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/501,154

(22) Filed: Feb. 26, 2019

(51) Int. Cl.
*A01H 7/00* (2006.01)
*A01H 9/00* (2006.01)

(52) U.S. Cl.
USPC ..... Plt./214

(58) Field of Classification Search
USPC ..... Plt./213, 214
See application file for complete search history.

*Primary Examiner* — Susan McCormick Ewoldt
(74) *Attorney, Agent, or Firm* — Cassandra Bright

(57) ABSTRACT

A new and distinct *Juniperus* cultivar named 'SMNJCHM' is disclosed, characterized by a compact, low growing mounding plant form and dense foliage. Plants are deer resistant and tolerate drought. The new cultivar is a *Juniperus chinensis*, suitable for ornamental garden purposes.

2 Drawing Sheets

Latin name of the genus and species: *Juniperus chinensis*.
Variety denomination: 'SMNJCHM'.

BACKGROUND OF THE INVENTION

The new cultivar is a product of a naturally occurring mutation. This new variety, hereinafter referred to as 'SMNJCHM', was selected as a single branch mutation of the unpatented *Juniperus chinensis* 'Hetzii'. The new variety was discovered by the inventor Timothy Wood in a commercial nursery in Grand Haven, Mich. in 2010.

After identifying the new variety as a potentially interesting selection, softwood cuttings were taken at the same nursery in Grand Haven, Mich., in 2010. The inventor continued controlled testing and propagation, assessing stability of the unique characteristics of this variety. At least four generations have been reproduced and have shown that the unique features of this cultivar are stable and reproduced true to type. First public access to plants of the variety occurred during August of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'SMNJCHM' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNJCHM' These characteristics in combination distinguish 'SMNJCHM' as a new and distinct *Juniperus* cultivar:

1. Low-growing, mounding plant form.
2. Dense foliage.
3. Attractive green and blue-green color.

4. Drought tolerant.
5. Deer resistant.

COMPARISON TO PARENT VARIETY

'SMNJCHM' is similar in most horticultural characteristics to the parent variety. Plants of the new cultivar 'SMNJCHM' however, differ in the following:

1. New variety has more green foliage, while parent has more blue foliage.
2. New variety has a more compact and dense plant habit than the parent.

COMMERCIAL COMPARISON

In addition to the parent, 'SMNJCHM' can be compared to the commercial variety *Juniperus chinensis* 'Blue Pfitzer', unpatented. The varieties are similar in most horticultural characteristics, however, plants of 'SMNJCHM' differ in the following:

1. New cultivar has more green foliage; comparator has more blue foliage.
2. New variety is more compact and rounded than this comparator.

BRIEF DESCRIPTION OF THE PHOTOGRAPHS

Figure 1:
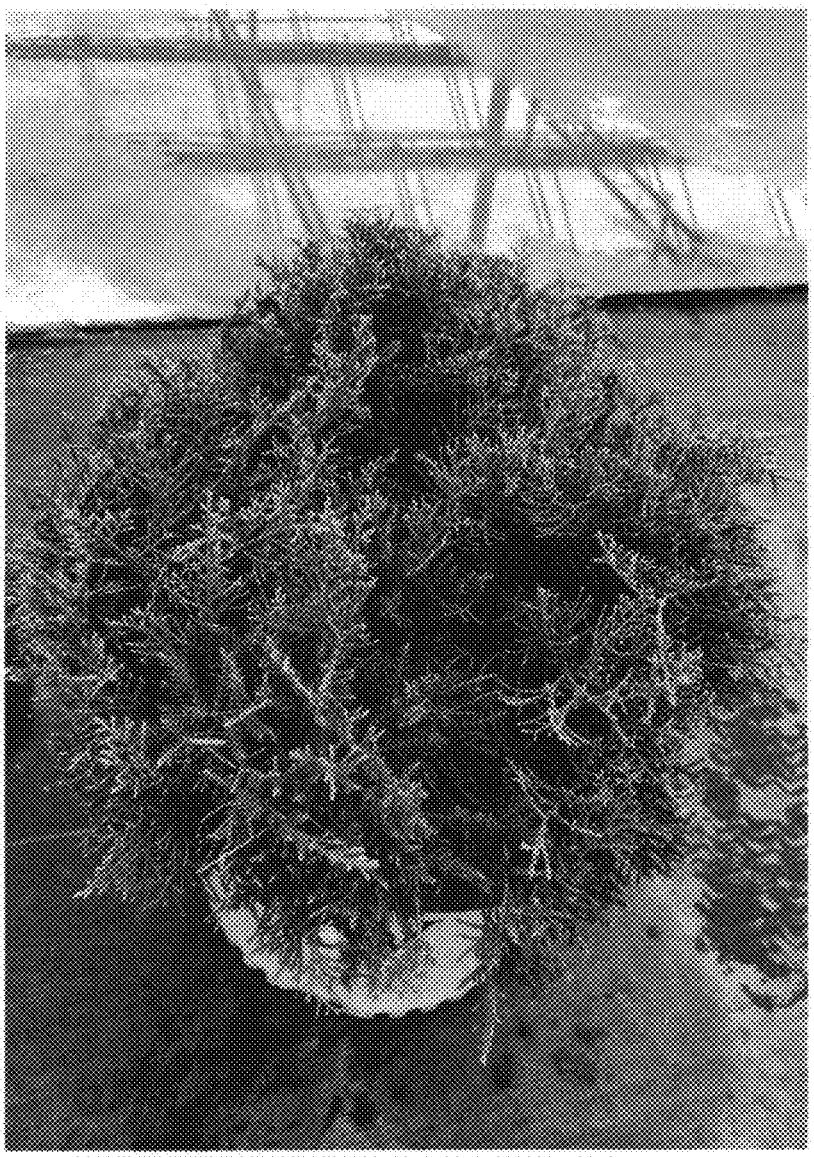

The accompanying photograph in FIG. 1 illustrates in full color a typical plant of 'SMNJCHM' grown outdoors in Grand Haven, Mich. The plant is approximately 2-3 years old, and is shown in a #3 size container.

Figure 2:
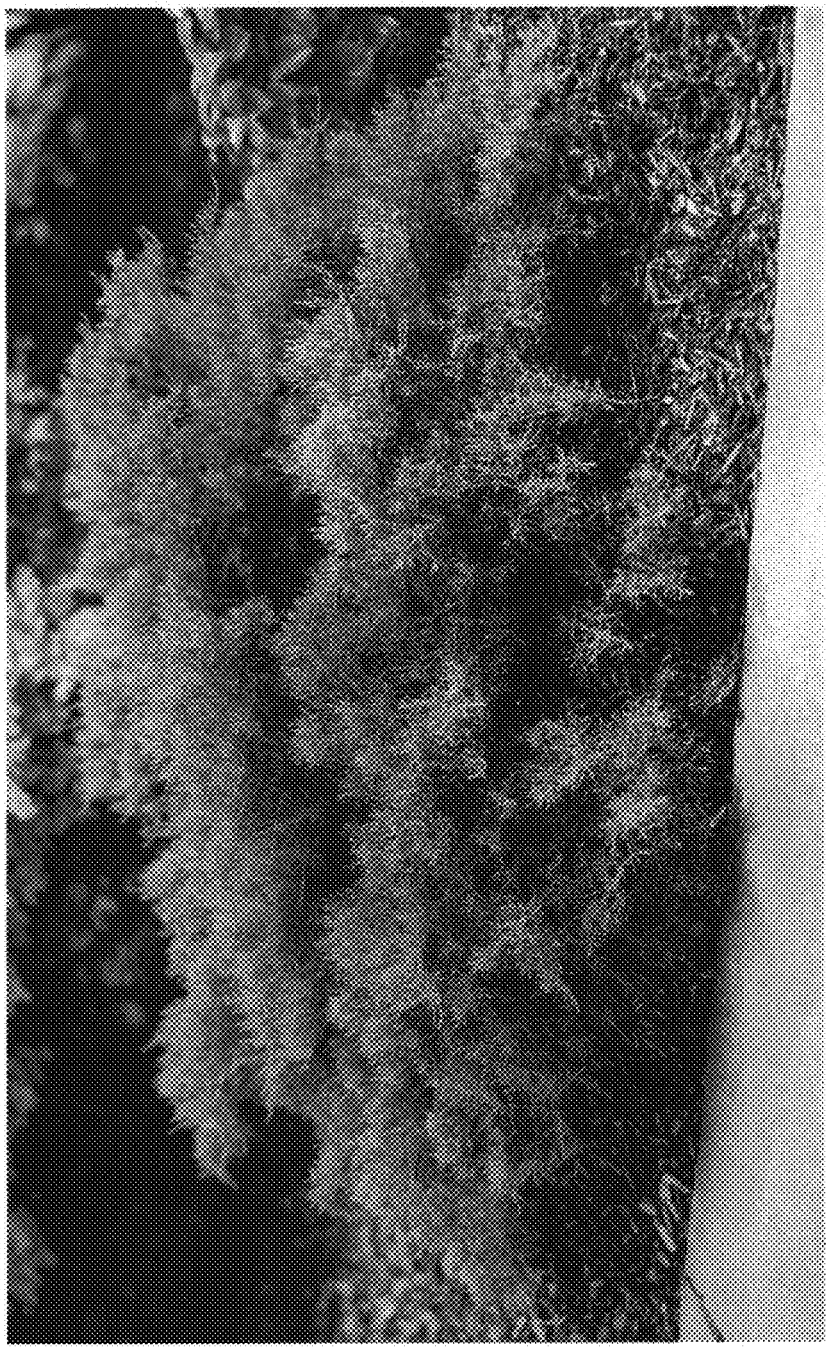

FIG. 2 illustrates a mature plant planted outdoors in a trial garden at approximately 8 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNJCHM' plants grown outdoors in Grand Haven, Mich. Plants are approximately 1-3 years old, in a 3 size container. Measurements and numerical values represent averages of typical plant types.

Botanical classification: *Juniperus chinensis* 'SMNJCHM'.

PROPAGATION

Time to rooting: 90 days at approximately 24° F.

Time to produce a rooted cutting: Approximately 200 days.

Root description: Thick to thin, moderately dense, fibrous, moderately branched. Colored brown and white, not accurately measured by R.H.S. chart.

PLANT

Growth habit: Moderately vigorous to freely branching.

Height: 54 cm.

Plant spread: 82 cm.

Typical growth rate: Moderate.

Branching characteristics: Approximately 15 lateral branches. Lateral stems are held at an angle of 45 to 80 degrees from the main stem.

Stems:

*Color*.—New growth: RHS Greyed-Green 190A. Mature growth: RHS Greyed-Orange 177C.

*Appearance*.—Round with thorns.

*Strength*.—Strong and flexible.

*Texture*.—Scaly, with thorns.

Thorns:

*Length*.—5 mm.

*Color*.—New growth: RHS Greyed-Green 190A. Mature growth: RHS Greyed-Orange 177C.

Lateral branches:

*Length*.—Average 43 cm.

*Diameter*.—4 mm.

*Strength*.—Strong.

Internode length: Average 2.75 cm.

FOLIAGE

General description: Needle-like, imbricate, slightly appressed.

Leaf:

*Arrangement*.—Alternate and whorled.

*Type*.—Single.

*Shape of blade*.—Linear, needle-like.

*Average length*.—5 mm.

*Average width*.—1 mm.

*Apex*.—Acute.

*Base*.—Fused.

*Margin*.—Entire.

*Texture of top surface*.—Smooth.

*Texture of bottom surface*.—Smooth.

*Color*.—Young foliage upper side: RHS Green 143A. Newest, uppermost foliage on spray color near RHS Yellow-Green 151D. Young foliage under side: RHS Green 143C. Newest, uppermost foliage on spray color near RHS Yellow-Green 151D. Mature foliage upper side: RHS Green 143A, tinted Green 136C. Mature foliage under side: RHS Green 143C, tinted Green 136C.

*Venation*.—Linear, indistinguishable from leaf blade.

*Fragrance*.—Light evergreen.

Petiole:

*Length*.—2 mm.

*Diameter*.—1 mm.

*Texture, upper side*.—Smooth.

*Texture, under side*.—Smooth.

*Color, upper side*.—RHS Green 138B.

*Color, under side*.—RHS Green 138B.

FLOWER

Flowering not observed.

FRUIT

Not observed to date.

OTHER CHARACTERISTICS

Disease and pest resistance: Neither resistance nor susceptibility observed.

Drought tolerance: Good tolerance for drought.

Temperature tolerance: USDA Zones 4-8.

What is claimed is:

1. A new and distinct cultivar of *Juniperus* plant named 'SMNJCHM' as herein illustrated and described.

* * * * *